United States Patent
Trunk et al.

(10) Patent No.: US 7,658,949 B2
(45) Date of Patent: *Feb. 9, 2010

(54) SURFACE MODIFICATION OF LACTOSE EXCIPIENT FOR USE IN POWDERS FOR INHALATION

(75) Inventors: Michael Trunk, Ingelheim (DE);
Inga-Lis Timmermann, Kiel (DE);
Bernd Wilhelm Mueller, Flintbek (DE);
Hartwig Andreas Steckel, Schoenkirchen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 377 days.

This patent is subject to a terminal disclaimer.

(21) Appl. No.: 11/231,459

(22) Filed: Sep. 21, 2005

(65) Prior Publication Data

US 2006/0120970 A1 Jun. 8, 2006

(30) Foreign Application Priority Data

Oct. 1, 2004 (DE) .................. 10 2004 048 389

(51) Int. Cl.
*A61K 9/50* (2006.01)
*A61K 9/00* (2006.01)
*A61K 9/14* (2006.01)
*A61K 31/715* (2006.01)

(52) U.S. Cl. .................. 424/499; 424/400; 424/489; 514/53

(58) Field of Classification Search .......... 424/499, 424/400, 489; 514/53
See application file for complete search history.

(56) References Cited

U.S. PATENT DOCUMENTS

| 3,634,582 | A | 1/1972 | Hartley et al. |
| 5,478,578 | A | 12/1995 | Arnold et al. |
| 7,132,115 | B2 * | 11/2006 | Musa et al. ........... 424/499 |
| 2004/0062719 | A1 | 4/2004 | Buckton et al. |
| 2006/0025326 | A1 | 2/2006 | Lankinen et al. |

FOREIGN PATENT DOCUMENTS

| WO | WO 92/18110 A1 | 10/1992 |
| WO | WO 95/05805 A1 | 3/1995 |
| WO | WO 00/30265 A3 | 5/2000 |
| WO | WO 01 76560 A1 | 10/2001 |
| WO | WO 02 07705 A1 | 1/2002 |

(Continued)

OTHER PUBLICATIONS

Hogan, SE, Buckton, G (2001) The Application of Near Infrared Spectroscopy and Dynamic Vapor Sorption to Quantify Low Amorphous Contents of Crystalline Lactose, Pharmaceutical Research, vol. 18, No. 1, p. 112-116.*

(Continued)

*Primary Examiner*—Shaojia Anna Jiang
*Assistant Examiner*—Scarlett Goon
(74) *Attorney, Agent, or Firm*—Michael P. Morris; Mary-Ellen M. Devlin; Wendy A. Petka

(57) ABSTRACT

The invention relates to a process for the surface-energy passivation of lactose which is intended for use as an excipient in the production of inhalable powders, and the use of such optimised carrier materials in the manufacture of inhalable powders.

10 Claims, 1 Drawing Sheet

Aqua bidest. = twice-distilled water
Befeuchtungskammer = humidity chamber
Probe = sample Schematic structure of an RH perfusion cell

FOREIGN PATENT DOCUMENTS

| WO | WO 02/30389 A1 | 4/2002 |
| WO | WO 02/30390 A3 | 4/2002 |
| WO | WO 02/30928 A1 | 4/2002 |
| WO | WO 02/45682 A1 * | 6/2002 |
| WO | WO 03/000265 A1 | 1/2003 |
| WO | WO 03/017970 A1 | 3/2003 |
| WO | WO 03/017979 A1 | 3/2003 |

OTHER PUBLICATIONS

Sebhatu, T., Angberg, M., Ahlneck, C. (1994) Assessment of the degree of disorder in crystalline solids by isothermal microcalorimetry. International Journal of Pharmaceutics, vol. 104, p. 135-144.*

Briggner, L.-E., Buckton, G., Bystrom, K., Darcy, P. (1994) The use of isothermal microcalorimetry in the study of changes in crystallinity induced during the processing of powders. International Journal of Pharmaceutics, vol. 105, p. 125-135.*

Buckton, Graham et al, "The Use of Gravimetric Studies to Assess the Degree of Crystallinity of Predominantly Crystalline Powders", International Journal of Pharmaceutics, Amsterdam: Bd. 123, Nr. 2, 1995, pp. 265-271.

Naini, Venkatesh et al, "Physicochemical Stability of Crystalline Sugars and Their Spray-Dried Forms: Dependence Upon Relative Humidity and Suitability for Use in Powder Inhalers", Drug Development and Industrial Pharmacy, New York, New York: US, Bd. 24, Nr. 10, 1998, pp. 895-909.

Dilworth, Sarah E. et al, "Approaches to Determine the Enthalpy of Crystallisation, and Amorphous Content, of Lactose From Isothermal Calorimetric Data", International Journal of Pharmaceutics, Amsterdam NL: Bd. 284, Nr. 1-2, Sep. 11, 2004, pp. 83-94.

Berlin, E., et al. "Calorimetric Measurement of the Heat of Desorption of Water Vapor from Amorphous and Crystalline Lactose", Thermochimica Acta, Bd. 2, 1971, Elsevier Publishing Co., Amsterdam, pp. 150-152.

Steckel, Hartwig et al. "Calorimetric Study on Amorphous Lactose During and After Re-Crystallization at Different Relative Humidity", Pharmazeutische Industrie, 2005 Germany: Bd 67, Nr. 6 pp. 709-712.

Newell, Helen E. et al., The Use of Inverse Phase Gas Chromatography to Measure the Surface Energy of Crystalline, Amorphous, and Recently Milled Lactose, Pharmaceutical Research, vol. 18, No. 5, 2001, pp. 662-666, Plenum Publishing Corp., New York, USA.

Zeng, Xian Ming et al., The Influence of Lactose Carrier on the Content Homogeneity and Dispersability of Beclomethasone Dipropionate from Dry Powder Aerosols, International Journal of Pharmaceutics, vol. 197, 2000, pp. 41-52, Elsevier Science B.V., The Netherlands.

* cited by examiner

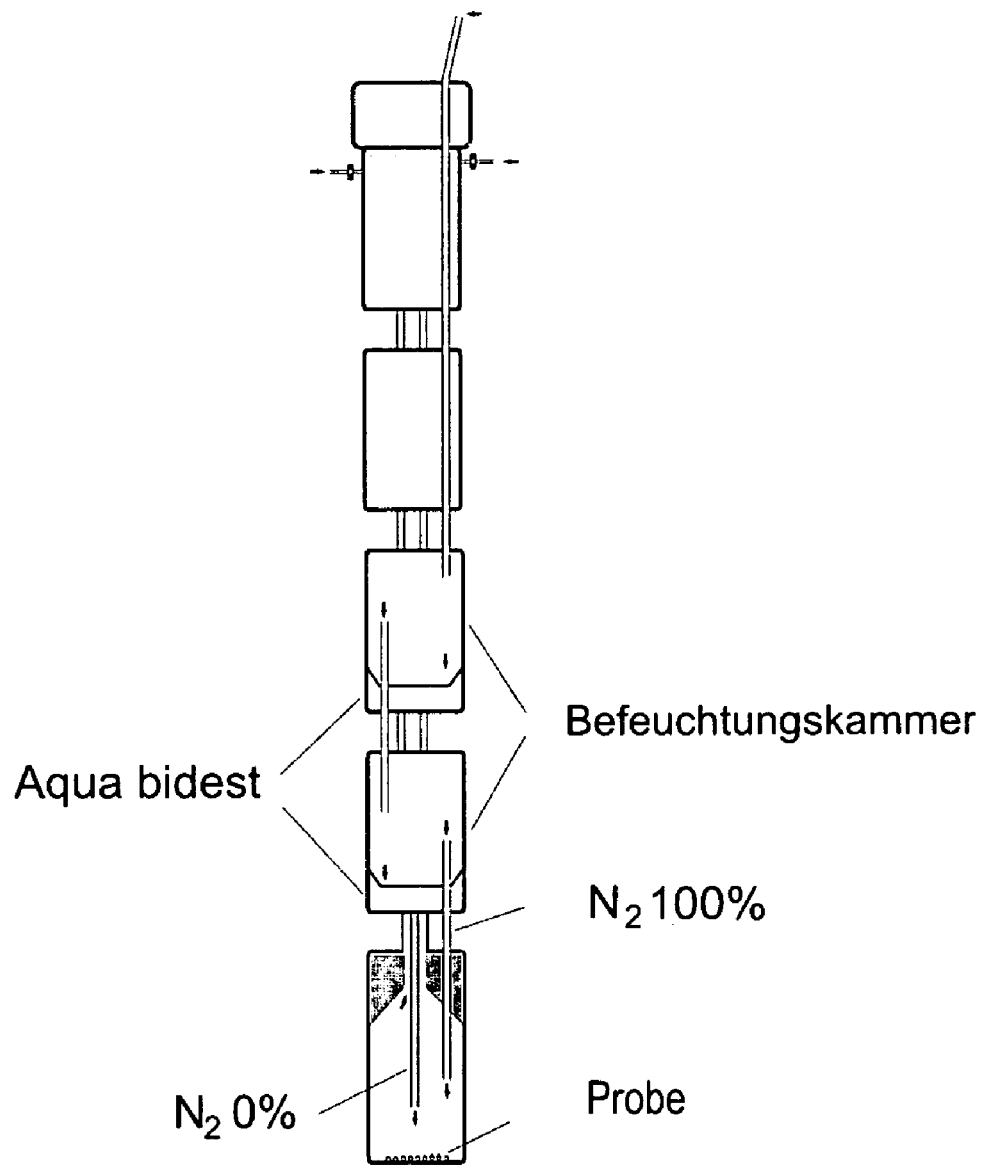
Aqua bidest. = twice-distilled water
Befeuchtungskammer = humidity chamber
Probe = sample
Figure 1: Schematic structure of an RH perfusion cell

SURFACE MODIFICATION OF LACTOSE EXCIPIENT FOR USE IN POWDERS FOR INHALATION

This application claims benefit to German application DE 10 2004 048 389, filed Oct. 1, 2004.

The invention relates to a process for the surface-energy passivation of lactose which is intended for use as an excipient in the production of inhalable powders, and the use of such optimised carrier materials in the manufacture of inhalable powders.

BACKGROUND TO THE INVENTION

Powdered inhalants, as prepared according to the prior art (for example DE-A-179 22 07), in addition to the chemical stability of the active substance and the composition of the medicament as such must above all have physically constant properties. This means specifically that the aerosol properties must remain constant in terms of their aerodynamic characteristics (e.g. aerodynamic particle size). This means that both for the micronised active substance and for the excipients used in the product the latter should be used in their most physico-chemically stable form. For lactose, this means, from a thermodynamic point of view, that this is true when it is in the form of alpha-lactose monohydrate under normal conditions. This is particularly true of the crystalline ordering of the surface of the particles.

It is known that when organic substances are ground, as a result of the significant input of mechanical energy, amorphous fractions may be produced or there may be changes in the crystalline structure leading to thermodynamically less stable modifications. It is also known that lactose may occur in various forms (Coenraad F. Lerk, Physikalisch-pharmazeutische Eigenschaften von Lactose, Pharmazie in unserer Zeit, 16, 1987, No. 2; 39-46).

For example amorphous lactose produced during the grinding of lactose or under other mechanical stress may be recrystallised by known technical methods (e.g. WO 92/18110 or WO 95/05805). However, these methods have the drawback that they only achieve breakdown of amorphous fractions such as occur after micronisation processes. However, these processes do not necessarily result in the breakdown of beta-lactose, which may also occur in these treatment processes, and during the large-scale industrial grinding of lactose to a particle size range with a value of $x_{50}>10$ μm. Thermodynamically unstable fractions such as beta-lactose, for example, even if they are only present on the surface of lactose, constitute a factor which may have a negative effect on the long-term and storage stability of an inhalable powder, for example.

The aim of the present invention is therefore to provide a process by which any thermodynamically less stable lactose fractions present, particularly fractions of beta-lactose, on the surface of crystalline lactose may be converted into alpha-lactose.

The detection of beta-lactose, for example on the surface of crystalline lactose, is analytically challenging, particularly when the amounts of beta-lactose are small.

The present invention therefore also sets out to provide a method of analysis which makes it possible to detect tiny amounts of beta-lactose in lactose crystals consisting predominantly of alpha-lactose.

DESCRIPTION OF DRAWINGS

FIG. 1 schematically shows the structure of an RH perfusion cell.

DESCRIPTION OF THE INVENTION

Surprisingly, it has been found that the recrystallisation process of thermodynamically labile lactose modifications adhering to the surface of lactose particles may be designed so that lactose is preferably formed in the form of the thermodynamically stable alpha-lactose monohydrate.

Accordingly, the present invention relates to a process for preparing lactose which contains exclusively alpha-lactose-monohydrate, characterised in that a lactose mixture which does not exclusively contain alpha-lactose-monohydrate is exposed to a relative humidity of at least 80% r.h.

By lactose mixtures are meant within the scope of the present invention lactose mixtures which do not exclusively contain alpha-lactose-monohydrate. Such lactose mixtures are, in particular, lactoses which have disordered crystal structures on their surface. Such lactose mixtures occur, for example, if lactose is subjected to a grinding process. In such a grinding process the input of energy destroys any pre-existing clearly defined crystalline structure of the lactose, resulting in the occurrence of different, to some extent amorphous modifications of the lactose. By lactose mixtures within the sense of the present invention are also meant lactoses which contain lactose in the form of beta-lactose.

Common lactose mixtures which are used in the process according to the invention also include, for example, those which are sold commercially by numerous manufacturers. Examples include the following grades of ground lactose sold by the company Meggle (e.g. Granulac 70, Granulac 140, Granulac 200, Granulac 230, Sorbolac 400), the company DMV (e.g. Pharmatose 150M, Pharmatose 200M, Respitose 200M, Pharmatose 350M), or the company Borculo (e.g. Lactochem Powder, Lactochem Fine Powder, Lactochem Coarse Powder, Lactochem Regular Powder, Lactochem Extra Fine Powder, Lactochem Super Fine Powder). Examples of commercially available screened grades which may be subjected as lactose mixtures to the process according to the invention, may be obtained from the company Meggle (e.g. Sacchelac 80, Sperolac 100, Inhalac 70, Inhalac 120, Inhalac 230), the company DMV (e.g. Pharmatose 125, Pharmatose 325M), or from the company Borculo (e.g. Lactochem Coarse Crystals, Lactochem Crystals, Lactochem Fine Crystals, Lactochem Extra Fine Crystals).

In a preferred embodiment of the process according to the invention the lactose mixture is exposed to the above-mentioned relative humidity for a period of at least 4 hours, preferably at least 6 hours, particularly preferably at least 12 hours, more preferably at least 18 hours.

Within the scope of the process according to the invention the action of moisture is preferably applied at a temperature of above 20° C., particularly preferably in a temperature range from 20-40° C., particularly preferably at 25-35° C., for example at 25° C., 30° C. or 35° C.

In a preferred embodiment of the process according to the invention, the lactose mixture is exposed to a relative humidity of at least 85% r.h., preferably at least 90% r.h., particularly preferably at least 93% r.h.

By the relative humidity (r.h.) is meant, within the scope of the present invention and in accordance with the prior art, the quotient of the partial pressure of the water vapour and the vapour pressure of the water at the temperature in question.

In preferred embodiments of the process according to the invention, moreover, the process is carried out a) by preparing the lactose mixture in such a way as to form the largest possible surface area for the powder bed, b) then exposing the lactose mixture to the above-mentioned climatic conditions of temperature and humidity;

c) and then reducing the relative humidity to which the lactose sample is exposed.

Preferably the surface area of the powder bed is only reduced after steps a and b have been carried out. Instead of simply reducing the relative humidity in step c, the relative humidity may for example also be adjusted to a value of less than 20% r.h. or less than 10% r.h. at elevated temperature.

By means of the process according to the invention in particular the surfaces of the lactose particles are modified such that lactose is formed in the form of its modification which is most thermodynamically stable under normal conditions, namely alpha-lactose monohydrate.

In a possible variant of the process according to the invention the conditioning step may be followed by a drying step in which excess process water is eliminated from the system. Drying may be carried out for example by reducing the relative humidity to less than 20%, preferably less than 15% while increasing the temperature (for example to 70° C., or 75° C. or 80° C. or 85° C.) as a function of a process time of at least 1 h, preferably at least 2 h. In an alternative embodiment the lactose product which is to be dried may also be exposed to an absolutely dry environment, possibly dry nitrogen with a residual moisture content of less than 5% r.h., in which case processing times of at least 6 h, preferably at least 12 h should be selected.

In another aspect the present invention relates to alpha-lactose which may be obtained by the process according to the invention. This is particularly characterised by its stoichiometric composition of water and lactose (=1:1). The crystal water is locked in and is not accessible up to temperatures of 80° C. The crystal water is only released completely, for example, above 100° C. to 120° C. By contrast, anhydrate forms of lactose such as for example beta-lactose or the ANhydrate form of alpha-lactose are characterised by hygroscopic behaviour, so that water which as a plasticiser accelerates the recrystallisation process can be released from crystalline anhydrate forms of lactose during subsequent drying. By comparison, after the end of the recrystallisation of lactose mixtures according to the invention, in alpha-lactose monohydrate the water incorporated in the crystal lattice is locked in so tightly that it is not released during a drying step. No additional water adsorptively bound to alpha-lactose monohydrate is observed.

The present invention further relates to the use of alpha-lactose which may be obtained by the process according to the invention as an excipient in the manufacture of an inhalable powder containing an active substance.

These inhalable powders containing an active substance may for example be obtained by processes described in the prior art, such as for example International Patent Applications WO 02/30390, WO 03/017970 or WO 03/017979.

The alpha-lactose which may be obtained by the manufacturing process according to the invention may be used generally as an excipient for preparing inhalable powders which contain active substances which from a therapeutic point of view should sensibly be administered by inhalation. Preferably active substances are used which are selected for example from among the betamimetics, anticholinergics, corticosteroids, PDEIV-inhibitors, EGFR-inhibitors and LTD4-antagonists or double or triple combinations thereof, such as for example combinations of anticholinergics with betamimetics, corticosteroids, PDEIV-inhibitors, EGFR-inhibitors or LTD4-antagonists, or combinations of betamimetics with corticosteroids, PDEIV-inhibitors, EGFR-inhibitors or LTD4-antagonists, or combinations of corticosteroids with PDEIV-inhibitors, EGFR-inhibitors or LTD4-antagonists or combinations of PDEIV-inhibitors with EGFR-inhibitors or LTD4-antagonists or combinations of EGFR-inhibitors with LTD4-antagonists. The invention also relates to the combinations of three active substances, each selected from one of the above categories of compounds.

Compounds used as betamimetics are preferably selected from among albuterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2 (3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the betamimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2

(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics, those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the preferred acid addition salts of the betamimetics are selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. Of the above-mentioned acid addition salts, the salts of hydrochloric acid, methanesulphonic acid, benzoic acid and acetic acid are particularly preferred according to the invention.

The anticholinergics used in the process according to the invention are preferably salts selected from among tiotropium salts, oxitropium salts, flutropium salts, ipratropium salts, glycopyrronium salts and trospium salts.

In the above-mentioned salts the cations tiotropium, oxitropium, flutropium, ipratropium, glycopyrronium and trospium are pharmacologically active ingredients. As anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodide and methanesulphonate are particularly preferred.

Of particular importance is tiotropium bromide. In the case of tiotropium bromide the drug combinations according to the invention preferably contain it in the form of the crystalline tiotropium bromide monohydrate which is known from WO 02/30928. If tiotropium bromide is used in the drug combinations according to the invention in anhydrous form it is preferable to use the anhydrous crystalline tiotropium bromide which is known from WO 03/000265.

The following compounds may preferably also be used as anticholinergics:
tropenol 2,2-diphenylpropionate-methobromide,
scopine 2,2-diphenylpropionate-methobromide,
scopine 2-fluoro-2,2-diphenylacetate-methobromide,
tropenol 2-fluoro-2,2-diphenylacetate-methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, optionally in the form of the solvates or hydrates thereof.

Within the scope of the present invention the term corticosteroids denotes compounds selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate and (S)-(2-oxo-tetrahydro-furan-3S-yl) 6α,9α-difluoro-11β-hydroxy-16α-methyl-3-oxo-17α-propionyloxy-androsta-1,4-dien-17β-carbothionate, optionally in the form of the racemates, enantiomers or diastereomers and optionally in the form of the salts and derivatives thereof, the solvates and/or hydrates thereof.

Particularly preferred is the steroid selected from among flunisolide, beclomethasone, triamcinolone, budesonide, fluticasone, mometasone, ciclesonide, rofleponide, ST-126, dexamethasone, (S)-fluoromethyl 6α,9α-difluoro-17α-[(2-furanylcarbonyl)oxy]-11β-hydroxy-16α-methyl-3-oxo-androsta-1,4-diene-17β-carbothionate and (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate, optionally in the form of the racemates, enantiomers or diastereomers and optionally in the form of the salts and derivatives thereof, the solvates and/or hydrates thereof.

Particularly preferred is the steroid selected from among budesonide, fluticasone, mometasone, ciclesonide and (S)-fluoromethyl 6α,9α-difluoro-17α-[(2-furanylcarbonyl)oxy]-11β-hydroxy-16α-methyl-3-oxo-androsta-1,4-diene-17β-carbothionate, optionally in the form of the racemates, enantiomers or diastereomers and optionally in the form of the salts and derivatives thereof, the solvates and/or hydrates thereof.

Any reference to steroids includes a reference to any salts or derivatives, hydrates or solvates thereof. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

Within the scope of the present invention the term PDEIV-inhibitors denotes compounds selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene] acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferred is the PDE IV-inhibitor selected from among enprofyllin, roflumilast, ariflo (cilomilast), AWD-12-281 (GW-842470), N-(3,5-dichloro-1-oxo-pyridin-4-yl)-4-difluoromethoxy-3-cyclopropylmethoxybenzamide, T-440, T-2585, arofyllin, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], PD-168787, atizoram, V-111294A, Cl-1018, CDC-801, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

Particularly preferred is the PDE IV-inhibitor selected from among roflumilast, ariflo (cilomilast), AWD-12-281 (GW-842470), arofyllin, 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], atizoram, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, of which roflumilast, Z-15370 and AWD-12-281 are of particular importance, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDEIV-inhibitors may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Within the scope of the present invention the term LTD4-antagonists denotes compounds selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1 R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

Particularly preferably the LTD4-antagonist is selected from among montelukast, pranlukast, zafirlukast, MCC-847 (ZD-3523), MN-001 and MEN-91507 (LM-1507), while montelukast, pranlukast and zafirlukast are particularly preferred, optionally in the form of the racemates, enantiomers or diastereomers thereof, optionally in the form of the pharmacologically acceptable acid addition salts as well as optionally in the form of the salts and derivatives thereof, the solvates and/or hydrates thereof.

By acid addition salts with pharmacologically acceptable acids which the above-mentioned LTD4-antagonists may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

By salts or derivatives which the above-mentioned LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Within the scope of the present invention the term EGFR-inhibitors denotes compounds selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo- 2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy)-7-methoxy-quinazoline, 4-[(3-chloro-4-fluoro-phenyl)amino]-6-[cis-4-(N-acetyl-N-methylamino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, cetuximab, trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluorophenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-

6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methane-sulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and cetuximab, optionally in the form of the racemates, enantiomers or diastereomers thereof, optionally in the form of the pharmacologically acceptable acid addition salts, the solvates and/or hydrates thereof.

It is particularly preferable within the scope of the present invention to use those EGFR inhibitors which are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)

carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxyethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

Particularly preferred as EGFR-inhibitors according to the invention are those compounds which are selected from among 4-[(3-chloro-4-fluorophenyl)amino]-6-{[4-(morpholin-4-yl)-1-oxo-2-buten-1-yl]-amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yl-oxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline, optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the above-mentioned EGFR-inhibitors may optionally be capable of forming are meant, for example, salts selected from among hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

The present invention therefore also relates to inhalable powders which contain as excipient, in addition to one or more of the above-mentioned active substances, the alpha-lactose-monohydrate which may be obtained according to the invention.

Moreover the present invention relates to the use of the alpha-lactose monohydrate which may be obtained by the process according to the invention for preparing a pharmaceutical composition for the treatment of ailments in which the administration by inhalation of medicaments containing active substance may provide a therapeutic benefit. Moreover the present invention relates to the use of the alpha-lactose monohydrate obtainable by the process according to the invention for preparing an inhalable powder containing an active substance.

In another aspect the present invention relates to a process for analytically determining amounts of crystalline forms of lactose which are different from alpha-lactose-monohydrate as well as optionally amorphous forms of lactose on the surface of alpha-lactose-monohydrate particles. Using this analytical process according to the invention it is also possible for example to detect the absence of beta-lactose by determining the desorption heat (or desorption enthalpy). Surprisingly, it has been found that measurement of the desorption heat which is produced when crystalline lactose releases hygroscopically/superficially adsorbed water can be used as a marker as to the nature of the crystalline surface composition of solid lactose particles. The amount which can be quantitatively measured serves as an evaluation magnitude for judging whether the sample consists of alpha-lactose monohydrate with regard to the polymorphic composition of the particle surface, or whether other fractions of crystalline and possibly also amorphous forms of lactose are also present.

Accordingly, the present invention also relates to a process for detecting any amounts of optionally crystalline forms of lactose other than alpha-lactose-monohydrate as well as optionally amorphous forms of lactose on the particle surface of alpha-lactose-monohydrate particles, characterised in that the desorption heat of a lactose mixture is determined.

A lactose obtained by the process according to the invention is characterised in that it typically has a desorption heat (or desorption enthalpy) of less than 60 J/g, preferably less than 40 J/g.

EXPERIMENTAL SECTION

The process according to the invention was tested using specific lactose mixtures. One of these specific lactose mixtures is referred to within the scope of the present invention as "lactose mix ABA". It is a mixture of alpha-lactose monohydrate Pharmatose 325M (manufacturer: DMV), beta-lactose of the grade Pharmatose DCL21 (manufacturer DMV) and spray-dried amorphous lactose (15%). The spray-dried lactose was obtained by common spray-drying processes known in the art.

The desorption enthalpy was determined for the lactose mixture ABA. The amounts weighed out were such that the recrystallisation peak was still visible. In order to determine the desorption enthalpy of the lactose mix ABA, 210 mg were weighed out, corresponding to an amorphous fraction of 2.1 mg in the one percent mix, 16.8 mg in the eight percent mix and 31.5 mg in the fifteen percent mix. If a sample was recrystallised even before the measurement, only sorption could be observed at the beginning of the experiment and desorption at the end. Recrystallised samples in the RH perfusion cell (FIG. 1) behave like crystalline samples, so that no exothermic recrystallisation peak and no endothermic desorption are measured. The advantage of this is that the integrated desorption surface for determining the desorption enthalpy is formed only by the desorption of the water from the recrystallised fraction and not by the carrier.

With regard to the analytical process according to the invention for determining beta-lactose the following procedure may be used, in particular.

In order to determine the desorption enthalpy of a sample a microcalorimeter with a room humidity perfusion cell (within the scope of this invention also referred to as an RH perfusion cell) may be used (cf. FIG. 1).

The RH perfusion unit consists of two humidity chambers and a steel ampoule in which the reaction takes place. Dry nitrogen (5.0; Messer Griesheim GmbH; Krefeld) is piped into the RH perfusion unit and divided into two gas currents by a flow-switch valve. One of the gas currents flows through the humidity chambers which are filled with 1.5 ml of twice-distilled aqua (distilled water) and, once the current is saturated, into the steel ampoule ($N_2$ 100%). The other gas current is passed outside the humidity chambers into the steel ampoule ($N_2$ O %). By controlling the flow-switch valve using a switching unit (e.g. a TAM Accessory Interface 2280 made by the company Thermometric, Sweden) the duration of opening of the valve is pre-set according to the programmed relative humidity, so that either the moist ($N_2$ 100%) or the dry nitrogen current ($N_2$ O %) passes into the steel ampoule. As a result of the ratio of dry to moist $N_2$ current, the desired relative humidity is established in the steel ampoule. In order to operate the RH perfusion unit with nitrogen, the flow volume of the nitrogen must be lowered to 3 ml/min. A pressure reducer (e.g. Hercules type), in conjunction with a very fine metering valve (e.g. type B-SS-2, made by Swagelok, cv 0.0004) may be fitted in order to reduce the flow volume to this slight flow. In order to operate the RH perfusion cell the flow volume is adjusted so as to be below 3 ml/min.

The RH perfusion cell is installed in the measuring cell and the operator waits until the signal from the microcalorimeter approaches the base line again. As soon as the signal indicates a heat flow (Q) of less than 100 µW, a programme for the RH perfusion cell can be started up.

The method to be used for the RH perfusion cell consists of three parts (see Table 1). In the first part the steel ampoule is adjusted to the desired climate, purged with dry nitrogen and a base line is recorded. The second pause in the first part only occurs if the base line is stable for longer than 10 min. During the pause the RH perfusion unit is taken from the measuring cell, the sample is weighed into the steel ampoule and sealed tightly. After a period of exactly thirty minutes after the lowering of the RH perfusion unit into the measuring cell, the experiment is restarted manually. In the second part first of all the sample is purged for a period of 240 min with a dry nitrogen current (0% r.h.). After drying, the step from 0% r.h. to the relative humidity laid down in the programme occurs automatically within a few minutes. The duration of Main II and Pause II depends on the mass of the amorphous fraction of the sample weighed in and the time the cell takes to return to the base line after the recrystallisation and desorption. In the third part the relative humidity is reset to 0% r.h., by purging the sample only with the dry nitrogen current. Using suitable software (e.g. Digitam Software Version 4.1; Messrs Thermometric) the measurement data recorded are input into a suitable computer programme (e.g. Origin Pro G7, Origin-Lab Corporation, USA) and evaluated.

In order to determine desorption enthalpy the heat flow (Q) (from 2nd part onwards, Main I) is plotted in a graph against the time (t), the base line is drawn on, subtracted and the area formed under the base line is integrated. This heat energy calculated (mJ) is based on the amorphous fraction (mg), in order to calculate the desorption enthalpy (J/g). The desorption enthalpy has a minus sign, as it is an endothermal process.

TABLE 1

Process of measurement with the RH perfusion unit

| Part | Step | Duration | RH | Steel ampoule |
|---|---|---|---|---|
| 1. | Pause | 20 min | 0% | empty |
|  | Baseline | 10 min | 0% | empty |
|  | Pause | — |  | weighing of sample |
| 2. | Main I | 90 min | 0% | drying of sample |
|  | Pause I | 150–240 min | 0% | drying of sample |
|  | Main II | depending on method | step up to 33%, , 45%, 58%/60% 75%, 80%; 90%; or 100% without time delay | sorption of sample |
|  | Pause II | depending on method | maintained at 33%, , 45%, 60% 75%, 80%; 90%; or 100% | recrystallisation and desorption of the amorphous fraction |
| 3. | Baseline | 60 min | step up to 0% | desorption of the sample |

The invention claimed is:

1. A process for preparing lactose which contains exclusively alpha-lactose-monohydrate, comprising exposing a lactose mixture which does not exclusively contain alpha-lactose-monohydrate to a relative humidity (r.h.) of at least 85% r.h., at a temperature in the range from 20 to 40° C., for a period of at least 4 hours to provide a lactose which contains exclusively alpha-lactose-monohydrate having a desorption heat of less than 40 J/g.

2. The process according to claim 1, wherein the lactose mixture which does not exclusively contain alpha-lactose-monohydrate is exposed to the relative humidity at a temperature of more than 20° C.

3. The process according to claim 1, wherein the exposure of the lactose mixture which does not exclusively contain alpha-lactose-monohydrate to a relative humidity of at least 85% r.h. includes forming the lactose mixture which does not exclusively contain alpha-lactose-monohydrate in a powder bed with a largest possible surface area for the powdered bed, exposing the lactose mixture which does not exclusively contain alpha-lactose-monohydrate to the relative humidity of at least 85% r.h., and then reducing the relative humidity to which the lactose mixture is exposed.

4. An alpha-lactose-monohydrate obtained by the process according to claim 1, wherein said alpha-lactose-monohydrate has a desorption heat of less than 40 J/g.

5. A method of preparing an inhalable powder containing an active substance, the method comprising:
exposing a lactose mixture which does not exclusively contain alpha-lactose-monohydrate to a relative humidity of at least 85% r.h., at a temperature in the range from 20 to 40° C., for a period of at least 4 hours, to provide a lactose which contains exclusively alpha-lactose-monohydrate having a desorption heat of less than 40 J/g; and
combining the active substance with the alpha-lactose-monohydrate.

6. An inhalable powder comprising at least one active substance and an alpha-lactose-monohydrate having a desorption heat of less than 40 J/g obtained by the process according to claim 5.

7. The inhalable powder of claim 6, wherein the active substance is selected from the group consisting of betamimetics, anticholinergics, corticosteroids, PDEIV-inhibitors, EGFR-inhibitors, LTD4-antagonists and combinations thereof.

8. The process according to claim 1, wherein the lactose mixture which does not exclusively contain alpha-lactose-monohydrate is exposed to a relative humidity of at least 90% r.h.

9. The process according to claim 1, wherein the lactose mixture which does not exclusively contain alpha-lactose-monohydrate is exposed to the relative humidity at a temperature in the range from 25 to 35° C.

10. The process according to claim 1, wherein the lactose mixture which does not exclusively contain alpha-lactose-monohydrate is exposed to a relative humidity of at least 93% r.h.

* * * * *